United States Patent
Jerussi et al.

(10) Patent No.: US 6,620,851 B2
(45) Date of Patent: Sep. 16, 2003

(54) METHODS FOR THE TREATMENT OF NEUROPATHIC PAIN AND OTHER DISORDERS USING R(−)-KETOPROFEN

(75) Inventors: Thomas P. Jerussi, Framingham, MA (US); Paul D. Rubin, Sudbury, MA (US)

(73) Assignee: Sepracor, Inc., Marlborough, MA (US)

( * ) Notice: Subject to any disclaimer, the term of this patent is extended or adjusted under 35 U.S.C. 154(b) by 11 days.

(21) Appl. No.: 10/062,766

(22) Filed: Feb. 5, 2002

(65) Prior Publication Data

US 2002/0147238 A1 Oct. 10, 2002

Related U.S. Application Data

(62) Division of application No. 09/507,470, filed on Feb. 22, 2000, now Pat. No. 6,362,227.
(60) Provisional application No. 60/122,382, filed on Mar. 2, 1999.

(51) Int. Cl.[7] ............................................... A61K 31/19
(52) U.S. Cl. ........................................................ 514/570
(58) Field of Search .......................................... 514/570

(56) References Cited

U.S. PATENT DOCUMENTS

| | | |
|---|---|---|
| 4,735,968 A | 4/1988 | Guth |
| 4,954,486 A | 9/1990 | Guth |
| 4,985,456 A | 1/1991 | Shimizu et al. |
| 5,331,000 A * | 7/1994 | Young et al. ............... 514/570 |
| 5,668,117 A | 9/1997 | Shapiro |
| 5,767,157 A | 6/1998 | Van Moerkerken |
| 5,840,723 A | 11/1998 | Sands |
| 5,863,927 A | 1/1999 | Smith et al. |
| 5,863,941 A | 1/1999 | Liedtke |
| 5,885,597 A | 3/1999 | Botknecht et al. |
| 5,968,519 A | 10/1999 | Youssefyeh et al. |

OTHER PUBLICATIONS

De Beaurepaire et al. "Anatomical mapping of brain sites involved in the antinociceptive effects of ketoprofen" Brain Research 1990, 536(1–2), pp. 201–206, abstract.*
Wang et al. "Spinal analgesic effect of ketoprofen and its mechanism" Zhongguo Yaolixue Tongbao, 1998, 14(3), pp. 251–253. abstract.*
Breivik, "Pain management" Bailliere's Clinical Anaesthesiology, 1994, 8/4, pp. 775–795, abstract.*
Seligmann, et al., "Drug–Induced Tinnitus and Other Hearing Disorders" *Drug Safety,* 14(3):198–212 (Mar. 1996).
Johnson et al., "Effects of Droperidol in Management of Vestibular Disorders", *Laryngoscope* 86(7):946–954 (1976).
Mendelson et al., "Human Laboratory Studies of Buprenorphine", *NIDA Res..Monogr. Ser.* 121:38–60 (1992).
Murai et al., Review of Pharmacologic Treatment of Tinnitus, *Am. Jour. of Otology,* 13(5):454–464, (Sep. 1992).
Sahley et al., "Naloxone Blockage of (−) Pentazocine–Induced Changes in Auditory Function", *Ear & Hearing,* 17(4):341–353 (1996).
Sahley et al., Blockage of Opioid–Induced Changes in Auditory Function at the Level of the Cochlea,*Ear & Hearing,* 17(6):552–558 (1996).
Leif Lyttkens, Pharmacological Treatment of Tinnitus with Special Reference to the Role of Melanin, *Scand, Audiol. Suppl. (Sweden)* 26:27–31 (1986).
N. Seppa, Tinnitus Location Found in the Brain, *Science News Online* (Jan. 24, 1998).

* cited by examiner

*Primary Examiner*—Theodore J. Criares
*Assistant Examiner*—Jennifer Kim
(74) *Attorney, Agent, or Firm*—Pennie & Edmonds LLP

(57) ABSTRACT

Methods of treating neuropathic pain, tinnitus, and related disorders are disclosed. These methods comprise the administration of optically pure R(−)-ketoprofen. Also disclosed are pharmaceutical compositions useful in the treatment of neuropathic pain and tinnitus which comprise optically pure R(−)-ketoprofen.

13 Claims, No Drawings

METHODS FOR THE TREATMENT OF NEUROPATHIC PAIN AND OTHER DISORDERS USING R(−)-KETOPROFEN

This is a division of application No. 09/507,470, filed Feb. 22, 2000 now U.S. Pat. No. 6,362,227 which claims benefit of Provisional Application No. 60/122,382, filed Mar. 2, 1999.

1. FIELD OF THE INVENTION

The invention relates to methods of treating neuropathic pain, tinnitus, and other disorders, and to pharmaceutical compositions useful in the treatment of neuropathic pain and tinnitus.

2. BACKGROUND OF THE INVENTION

2.1. KETOPROFEN AND ITS ISOMERS

Chemically, ketoprofen is 2-(3-benzoylphenyl)-propionic acid, and has the following structure:

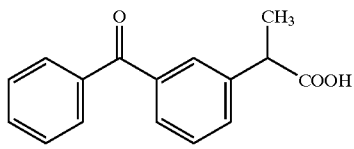

Racemic ketoprofen (a mixture of the R(−) and S(+) enantiomers) is sold under the tradenames Orudis® and Oruvail® for the treatment of inflammation. *Physicians' Desk Reference* 52$^{nd}$ Ed., p. 3092 (1998). Generally, ketoprofen is considered to be a nonsteroidal anti-inflammatory agent ("NSAID"). NSAIDs are believed to exhibit activity as COX-1 or COX-2 enzyme inhibitors. Most NSAIDs are believed to cause gastrointestinal irritation.

The S(+) enantiomer of ketoprofen has long been thought to possess most, if not all, of the pharmacological activity of the racemate. See, e.g., Yamaguchi et al., *Nippon Yakurigaku Zasshi*. 90:295–302 (1987); Abas et al., *J. Pharinacol. Exp. Ther.*, 240:637–641 (1987); and Caldwell et al., *Biochem. Pharrnacol.* 37:105–114 (1988). Indeed, U.S. Pat. Nos. 4,868,214, 4,962,124, and 4,927,854 each allege that the analgesic activity of ketoprofen resides exclusively in the S(+) enantiomer.

However, U.S. Pat. No. 5,331,000 discloses the use of the optically pure R(−) enantiomer as an antipyretic and analgesic agent to treat, with reduced gastrointestinal irritancy.

2.2. NEUROPATHIC PAIN

The effective treatment of pain requires an understanding of its physiology. It is well known, however, that stimuli which activate pain receptors in one tissue may not activate pain receptors in another. For example, pricking or cutting which causes pain in skin tissue does not cause pain in the stomach or intestine. The causes of pain in skeletal muscle, joints, and arteries can also differ. *Principles of Neurology*, 6$^{th}$ ed., Adams, R. D., et al., eds. (McGraw-Hill: 1997), pp. 133–134. Consequently, methods useful for relieving one type of pain are often less effective, or even ineffective, when applied to the alleviation of others.

In general, neuropathic pain is persistent and is characterized by burning, gnawing, aching, shooting, or lancinating sensations. It is frequently associated with hyperesthesia, hyperalgesia, allodynia, and hyperpathia, and in some cases by sensory deficit or autonomic dysfunction. Unfortunately, and unlike other types of pain, neuropathic-pain tends to respond poorly to analgesic medication. *Principles of Neurology*, 6$^{th}$ ed., Adams, R. D., et al., eds. (McGraw-Hill: 1997), p. 140.

Depending on the particular nerves involved, a particular instance of neuropathic pain can be classified as a central or peripheral neuropathy. Central neuropathies arise from spinal cord, brainstem, thalamic, and cerebral damage or disease, while peripheral neuropathies arise from damage or disease of peripheral nerves. Specific peripheral neuropathies include, but are not limited to: thoracic outlet obstruction syndromes; compression and entrapment neuropathies such as ulnar nerve palsey, carpal tunnel syndrome, peroneal nerve palsey, radial nerve palsey; and Guillain-Barré syndrome. *The Merck Manual*, 16th ed., 1518–1522 (1992).

Neuropathic, or neurogenic, pain arises from the direct stimulation of nervous tissue. Neuropathic pain encompasses a wide variety of disorders involving single and multiple nerves. These include, but are not limited to, trigeminal neuralgia and disorders due to herpes zoster, diabetes, and trauma (including causalgia); spinal arachnoiditis and spinal cord injuries; and the thalamic pain syndrome of Déjerine-Roussy. *Principles of Neurology*, 6$^{th}$ ed., Adams, R. D., et al., eds. McGraw-Hill: 1997), p. 140.

Neuropathic pain is caused by a variety of factors including, but not limited to: trauma caused by injury or surgical operation; tumors; bony hyperostosis; casts; crutches; prolonged cramped postures; hemorrhage into a nerve; exposure to cold or radiation; collagen-vascular disorders; metabolic diseases such as diabetes; infectious diseases such as Lyme disease and HIV; toxins such as emetine, hexobarbital, barbital, chlorobutanol, sulfonamides, phenytoin, nitrofurantoin, the vinca alkaloids, heavy metals, carbon monoxide, triorthocresylphosphate, orthodinitrophenol, and other solvents and industrial poisons; autoimmune reactions; nutritional deficiency, and vitamin B deficiency in particular; and metabolic disorders such as hypothyroidism, porphyria, sarcoidosis, amyloidosis, uremia and diabetes. *The Merck Manual*, 16th ed., 1518 (1992).

Because so many causes of neuropathic pain exist, and because it tends to respond poorly to analgesic medication, the discovery of drugs that safely and effectively aid in its relief has been difficult.

2.3. TINNITUS

Like neuropathic pain, tinnitus is often thought of as a subjective disorder; numerous causes have thus been postulated for it. A patient with tinnitus typically perceives a sound in the head or the ears without an evident external stimulus. Such sounds often have a buzzing, ringing, roaring, whistling, or hissing quality, or may be more complex and vary over time. Vesterager, V., *BMJ*, 314:728–31 (1997).

Tinnitus can result from nearly all ear disorders, including, but not limited to: obstruction of the external auditory canal; infectious processes such as external otitis, myrignitis, otitis media, labyrinthitis, petrositis, syphilis and meningitis; eustachian tube obstruction; otosclerosis; middle ear neoplasms such as the glomus tympanicum and glomus jugulare tumors; Meniere's disease; arachnoiditis; cerebellopontine angle tumors; cardiovascular diseases such as hypertension, arteriosclerosis and aneurysms; anemia; hypothyroidism; hereditary sensorineural or noise-induced hearing loss; and acoustic trauma. *The Merck Manual*, 16th ed., 2324 (1992). Tinnitus can also result from ototoxicity caused by acute intoxication or long-term administration or exposure to salicylates, quinine and its synthetic analogues, aminoglycoside antibiotics, diuretics, carbon monoxide, heavy metals, and other drugs or toxins. Seligmann, H., et al., *Drug Safety* 14(3):198–212 (1996). Psychological causes have also been suggested. Vesterager, V., *BMJ*, 314:728–31 (1997).

The biological mechanism which causes or relates to tinnitus remains unclear. Some researchers have suggested that it may result from a decrease of the normal GABAergic inhibitory influence of neurons in the inferior colliculus. Møller, A. R., *Am. J. Otology,* 18:577–585 (1997). Others have argued that the disorder results from pathological changes of neurons within the inner ear. See, e.g., Ehrenberger, K., and Felix, D., *Acta Otolaryngol* (Stockh), 115:236–240 (1995). It has also been suggested that tinnitus generation might be similar to the "gate theory" of pain. See, e.g., Murai, Kazuo, et al., *Am. J. Otology* 13(5):454–464 (1992); Sahley, T. L., et al., *Ear & Hearing* 17:341–353 (1996); and Sahley, T. L., et al., *Ear & Hearing* 17:552–558 (1996).

Because its mechanism is poorly understood, the discovery of drugs that are effective in the treatment of tinnitus has been slow. Some researchers have alleged that administration of the local anesthetic lidocaine can reduce symptoms of the disorder, but its alleged effectiveness is of short duration. Lyttkens, L., *Scand. Audiol. Suppl.* (Sweden) 26:27–31 (1986); and Murai, Kazuo, el al., *Am. J. Otology* 13(5):454–464 (1992). Other drugs alleged to be somewhat effective in the treatment of tinnitus include oxazepam, clonazepam, glutamic acid, streptomycin, and eperisone hydrochloride. Murai, Kazuo, et al., *Am. J. Otology* 13(5):454–464 (1992). Unfortunately, these and other drugs are allegedly effective in only a few patients. More important, those drugs that are reportedly the most effective (e.g., lidocaine, oxazepam and clonazepam) can cause a wide variety of adverse effects. These include, but are not limited to, numbness, tingling, light-headedness, blurred speech, nausea, dermatitis, uricarial exanthema, vomiting, tremor, visual disturbance, disequilibrium, rashes, headache, diplopia, sedation, and sleepiness. Murai, Kazuo, et al., *Am. J. Otology* 13(5):454–464 (1992). There thus exists a need for a safe and effective method of treating tinnitus.

3. SUMMARY OF THE INVENTION

The invention is directed to methods of treating or preventing neuropathic pain, tinnitus, and other disorders, as well as pharmaceutical compositions suitable for the treatment of neuropathic pain and tinnitus.

This invention encompasses the use of optically pure R(−)-ketoprofen for treating or preventing neuropathic pain, which is generally not treated by anti-inflammatory, analgesic, or antipyretic agents. Moreover, the invention encompasses the use of optically pure R(−)-ketoprofen to treat or prevent tinnitus or ringing in the ears, which has heretofore been notoriously difficult to treat with any therapeutic agent.

3.1. DEFINITIONS

As used herein, the term "mammal" includes human. The terms "human" and "patient" are used interchangeably herein.

As used herein, the term "treating neuropathic pain," means alleviating, ameliorating, reducing, or relieving at least one symptom of acute or chronic neuropathic pain. Symptoms of acute or chronic neuropathic pain include, but are not limited to, burning, gnawing, aching, shooting, or lancinating sensations, sensory deficit, and autonomic dysfunction.

As used herein, the term "treating tinnitus" means alleviating, ameliorating, reducing, or relieving at least one symptom of acute or chronic tinnitus. Symptoms of acute or chronic tinnitus include, but are not limited to, the hearing of buzzing, ringing, roaring, whistling, or hissing sounds.

As used herein, the term "patient at risk of tinnitus" means a patient who is suffering from a disease or condition that is associated with tinnitus. Diseases or conditions associated with tinnitus include, but are not limited to: obstruction of the external auditory canal; infectious processes including external otitis, myrignitis, otitis media, labyrinthitis, petrositis, syphilis and meningitis; eustachian tube obstruction; otosclerosis; middle ear neoplasms such as the glomus tympanicum and glomus jugulare tumors; Meniere's disease; arachnoiditis; cerebellopontine angle tumors; cardiovascular diseases including hypertension, arteriosclerosis and aneurysms; anemia; hypothyroidism; hereditary sensorineural or noise-induced hearing loss; acoustic trauma; ototoxicity caused by acute intoxication or long-term administration or exposure to drugs or toxins including salicylates, quinine and its synthetic analogues, aminoglycoside antibiotics, diuretics, carbon monoxide, and heavy metals; and psychological disorders.

As used herein, the term "substantially free of its S(+) enantiomer" means that the composition contains less than about 10% by weight S(+)-ketoprofen. Preferably, the term "substantially free of its S(+) enantiomer" means that the composition contains less than about 5% by weight S(+)-ketoprofen. Most preferably, the term "substantially free of its S(+) enantiomer" means that the composition contains less than about 1% by weight of S(+)-ketoprofen. These percentages are based upon the total amount of ketoprofen present in the composition. The terms "substantially optically pure R(−) enantiomer of ketoprofen" or "substantially optically pure R(−)-ketoprofen" and "optically pure R(−)-ketoprofen" or "optically pure R(−) enantiomer of ketoprofen" are also encompassed by the above-described amounts.

As used herein, the term "pharmaceutically acceptable salts" refers to salts prepared from pharmaceutically acceptable non-toxic organic or inorganic bases. Suitable organic bases include, but are not limited to, lysine, N,N'-dibenzylethylenediamine, chloroprocaine, choline, diethanolamine, ethylenediamine, meglumine (N-methylglucamine) and procaine. Suitable inorganic bases include, but are not limited to, alkaline and earth-alkaline metals such as aluminum, calcium, lithium, magnesium, potassium, sodium and zinc.

4. DETAILED DESCRIPTION OF THE INVENTION

The invention involves using optically pure R(−)-ketoprofen to effectively treat neuropathic pain, tinnitus, and related disorders. The invention encompasses treating these disorders without causing adverse effects associated with racemic ketoprofen. Adverse effects associated with racemic ketoprofen include, but are not limited to: gastrointestinal irritation such as dyspepsia, nausea, abdominal pain, diarrhea, constipation, flatulence, vomiting, and stomatitis; anorexia; headache; dizziness; CNS inhibition such as somnolence, malaise, and depression; CNS excitation such as insomnia and nervousness; hypertension; palpitation; tachycardia; congestive heart failure; peripheral vascular disease, and tinnitus.

A first embodiment of the invention encompasses a method of treating neuropathic pain in a mammal which comprises administering to a mammal in need of such treatment a therapeutically effective amount of substantially optically pure R(−)-ketoprofen, or a pharmaceutically acceptable salt, solvate, or clathrate thereof. Preferably, the therapeutically effective amount of substantially optically pure R(−)-ketoprofen, or pharmaceutically acceptable salt, solvate, or clathrate thereof, is between about 1 mg and about 2000 mg, more preferably between about 5 mg and about 1500 mg, and most preferably between about 10 mg and about 1000 mg. Preferably, the substantially optically pure R(−)-ketoprofen comprises less than about 10% by weight S(+)-ketoprofen, more preferably less that about 5% by weight S(+)-ketoprofen, and most preferably less than about 1% by weight S(+)-ketoprofen.

This embodiment of the invention encompasses a method of treating a central neuropathy in a mammal. Preferably, the central neuropathy arises from the damage or disease of the spinal cord, brainstem, thalamus, or cerebellum.

The first embodiment of the invention also encompasses a method of treating a peripheral neuropathy in a mammal. Preferred peripheral neuropathies include, but are not limited to: thoracic outlet obstruction syndromes; compression and entrapment neuropathies such as ulnar nerve palsey, carpal tunnel syndrome, peroneal nerve palsey, and radial nerve palsey; and Guillain-Barré syndrome.

This first embodiment of the invention further encompasses compositions adapted for the treatment of a mammal suffering from neuropathic pain which comprise a therapeutically effective amount of substantially optically pure R(−)-ketoprofen, or a pharmaceutically acceptable salt, solvate, or clathrate thereof, said amount being sufficient to alleviate at least one symptom of neuropathic pain. The embodiment encompasses single unit dosage forms of substantially optically pure R(−)-ketoprofen which comprise from about 1 mg to about 2000 mg, more preferably from about 5 mg to about 1500 mg, and most preferably from about 10 mg to about 1000 mg of optically pure R(−)-ketoprofen, or a pharmaceutically acceptable salt, solvate, or clathrate thereof. Preferably, the substantially optically pure R(−)-ketoprofen comprises less than about 10% by weight S(+)-ketoprofen, more preferably less that about 5% by weight S(+)-ketoprofen, and most preferably less than about 1% by weight S(+)-ketoprofen.

Another embodiment of the invention encompasses a method of treating or preventing tinnitus or ringing in the ear in a patient which comprises administering to a patient in need of such treatment a therapeutically effective amount of substantially optically pure R(−)-ketoprofen, or a pharmaceutically acceptable salt, solvate, or clathrate thereof. Preferably, the therapeutically effective amount of substantially optically pure R(−)-ketoprofen, or pharmaceutically acceptable salt, solvate, or clathrate thereof, is between about 1 mg and about 2000 mg, more preferably between about 5 mg and about 1500 mg, and most preferably between about 10 mg and about 1000 mg. Preferably, the substantially optically pure R(−)-ketoprofen comprises less than about 10% by weight S(+)-ketoprofen, more preferably less that about 5% by weight S(+)-ketoprofen, and most preferably less than about 1% by weight S(+)-ketoprofen.

This embodiment of the invention also encompasses a method of preventing tinnitus or ringing in the ear in a patient at risk of tinnitus.

This embodiment of the invention further encompasses a method of treating tinnitus or ringing in the ear associated with a disease or condition selected from the group consisting of: obstruction of the external auditory canal; infectious processes including external otitis, myringitis, otitis media, labyrinthitis, petrositis, syphilis and meningitis; eustachian tube obstruction; otosclerosis; middle ear neoplasms such as the glomus tympanicum and glomus jugulare tumors; Meniere's disease; arachnoiditis; cerebellopontine angle tumors; cardiovascular diseases including hypertension, arteriosclerosis and aneurysms; anemia; hypothyroidism; hereditary sensorineural or noise-induced hearing loss; acoustic trauma; ototoxicity caused by acute intoxication or long-term administration or exposure to drugs or toxins including salicylates, quinine and its synthetic analogues, aminoglycoside antibiotics, diuretics, carbon monoxide, and heavy metals; and psychological disorders.

This embodiment of the invention also includes compositions adapted for the treatment of a patient suffering from tinnitus which comprise a therapeutically effective amount of optically pure R(−)-ketoprofen or a pharmaceutically acceptable salt, solvate, or clathrate thereof, said amount being sufficient to alleviate at least one symptom of tinnitus. The embodiment encompasses single unit dosage forms of substantially optically pure R(−)-ketoprofen which comprise from about 1 mg to about 2000 mg, more preferably from about 5 mg to about 1500 mg, and most preferably from about 10 mg to about 1000 mg of optically pure R(−)-ketoprofen, or a pharmaceutically acceptable salt, solvate, or clathrate thereof. Preferably, the substantially optically pure R(−)-ketoprofen comprises less than about 10% by weight S(+)-ketoprofen, more preferably less that about 5% by weight S(+)-ketoprofen, and most preferably less than about 1% by weight S(+)-ketoprofen.

A final embodiment of the invention encompasses compositions comprising R(−)-ketoprofen and a pharmaceutically acceptable carrier.

4.1. SYNTHESIS AND PREPARATION

Racemic ketoprofen can be made by the method described in U.S. Pat. No. 3,641,127, which is hereby incorporated by reference. The R(−) enantiomer of ketoprofen can be readily obtained from the racemate using, for example, high performance liquid chromatography (HPLC) or an optically active resolving base. A preferred method of resolving the R(−) enantiomer is disclosed in U.S. Pat. No. 5,677,469, which is incorporated herein by reference. Other methods suitable for resolving R(−)-ketoprofen are disclosed by, for example, U.S. Pat. Nos. 4,983,765 and 4,973,745, both of which are incorporated herein by reference. See, also, Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N.Y, 1962); and Wilen, S. H., *Tables of Resolving Agents and Optical Resolutions* p. 268 (E. L. Eliel, Ed., Univ. of Notre Dame Press, Notre Dame, Ind., 1972).

Enzymatic biocatalytic resolution may also be used to isolate the optically pure R(−) enantiomer from racemic ketoprofen. See, e.g., U.S. Pat. Nos. 5,057,427, and 5,077,217, both of which are incorporated herein by reference. A preferred enzymatic method is disclosed by U.S. Pat. No. 5,457,051, which is also incorporated herein by reference.

Optically pure R(−)-ketoprofen can further be prepared from the corresponding acrylic acid by catalytic hydrogenation using a chiral catalyst. See, e.g., U.S. Pat. Nos.: 5,198,561; 5,202,473; 5,202,474; 5,233,084; and 5,097,064, all of which are incorporated herein by reference.

Pharmaceutically acceptable salts of R(−)-ketoprofen are readily made using techniques well known to those skilled in the art. Examples of such techniques, and the salts made therefrom, are disclosed by U.S. Pat. No. 5,808,069, which is incorporated herein by reference.

4.2. PHARMACEUTICAL COMPOSITIONS AND METHOD OF USE

The magnitude of a prophylactic or therapeutic dose of R(−)-ketoprofen (referred to herein as the "active ingredient") in the acute or chronic management of disease (i.e., neuropathic pain, tinnitus, or a related disorder) will vary with the severity of the condition to be treated and the route by which the drug is administered. The dose, and perhaps the dose frequency, will also vary according to the age, body weight, and response of the individual patient. In general, the total daily dose range of R(−)-ketoprofen is from about 1 mg to about 2000 mg, in single or divided doses. Preferably, a daily dose range should be between about 5 mg and about 1500 mg, in single or divided doses. More preferably, a daily dose range should be between about 10 mg and about 1000 mg, in single or divided doses. In managing the patient, the therapy should be initiated at a lower dose, perhaps about 1 mg to about 200 mg, and increased up to about 1000 mg or higher depending on the patient's global response. It is further recommended that infants, children, patients over 65 years, and those with impaired renal or hepatic function, initially receive low doses, and that they be titrated based on individual response (s) and blood level(s). It may be necessary to use dosages outside these ranges in some cases as will be apparent to those skilled in the art. Further, it is noted that the clinician or treating physician will know how and when to interrupt, adjust or terminate therapy in conjunction with individual patient response. The terms "therapeutic amount" and "therapeutically effective amount" are encompassed by the above-described dosage amounts and dose frequency schedules.

In practical use, optically pure R(−)-ketoprofen can be combined as the active ingredient in intimate admixture with a pharmaceutically acceptable carrier according to conventional pharmaceutical compounding techniques. The pharmaceutically acceptable carrier may take a wide variety of forms depending on the form of preparation desired for administration, e.g., oral, parenteral (including intravenous, subcutaneous, intrathecal, and intramuscular), transdermal, and topical. In preparing the compositions for oral dosage form, any of the usual pharmaceutical media or excipients may be employed. These include, for example, water, glycols, oils, alcohols, flavoring agents, preservatives, coloring agents and the like in the case of oral liquid preparations such as suspensions, elixirs and solutions; or aerosols; or excipients such as starches, sugars, microcrystalline cellulose, diluents, granulating agents, lubricants, binders, disintegrating agents and the like in the case of oral solid preparations such as powders, capsules, caplets, and tablets. Solid oral preparations are generally preferred over liquid ones. Because of their ease of administration, tablets and capsules represent the most advantageous oral dosage unit forms, in which case solid pharmaceutical pharmaceutically acceptable excipients are obviously employed. If desired, tablets may be coated by standard aqueous or nonaqueous techniques. Preferred solid oral preparations are tablets and capsules.

Pharmaceutical stabilizers may be used to stabilize compositions comprising optically pure R(−)-ketoprofen, or pharmaceutically acceptable salts, solvates, or clathrates thereof. Acceptable stabilizers include, but are not limited to, L-cysteine hydrochloride, glycine hydrochloride, malic acid, sodium metabsulfite, citric acid, tartaric acid, and L-cystine dihydrochloride. See, e.g., U.S. Pat. Nos.: 5,731,000; 5,763,493; 5;541,231; and 5,358,970, all of which are incorporated herein by reference.

In addition to the common dosage forms set out above, the active ingredient (i.e., optically pure R(−)-ketoprofen) can be administered by controlled release means and/or delivery devices capable of releasing the active ingredient at a rate required to maintain constant pharmacological activity for a desirable period of time. Such dosage forms provide a supply of a drug to the body during a predetermined period of time and thus maintain drug levels in the therapeutic range for longer periods of time than conventional non-controlled formulations. Examples of controlled release pharmaceutical compositions and delivery devices which may be adapted for the administration of the active ingredient of the invention are described in U.S. Pat. Nos.: 3,847,770; 3,916,899; 3,536,809; 3,598,123; 3,630,200; 4,008,719; 4,687,610; 4,769,027; 5,674,533; 5,059,595; 5,591,767; 5,120,548 ; 5,073,543; 5,639,476; 5,354,566; and 5,733,566, the disclosures of which are incorporated herein by reference.

Pharmaceutical compositions of the invention suitable for oral administration may be presented as discrete units such as capsules, cachets, caplets, or tablets or aerosol sprays, each containing a predetermined amount of the active ingredient as a powder, as granules, or as a solution or a suspension in an aqueous or non-aqueous liquid, an oil-in-water emulsion, or a water-in-oil liquid emulsion. Such compositions may be prepared by any of the methods of pharmacy which include the step of bringing into association the active ingredient with a pharmaceutically acceptable carrier which constitutes one or more necessary ingredients. In general, the compositions are prepared by uniformly and intimately admixing the active ingredient with a liquid pharmaceutically acceptable carrier or a finely divided solid pharmaceutically acceptable carrier, or both, and then, if necessary, shaping the product into the desired presentation. For example, a tablet may be prepared by compression or molding, optionally with one or more accessory ingredients. Compressed tablets may be prepared by compressing in a suitable machine the active ingredient in a free-flowing form such as powder or granules, optionally mixed with a binder, lubricant, inert diluent, disintegrating agent, and/or surface active or dispersing agent. Molded tablets may be made by molding in a suitable machine a mixture of the powdered compound moistened with an inert liquid diluent. Preferably, each tablet contains from about 0.5 mg to about 1000 mg of the active ingredient, and each cachet or capsule contains from about 0.5 mg to about 2000 mg of the active ingredient, more preferably from about 5 mg to about 1500 mg, and most preferably between about 10 mg and about 1000 mg.

The invention is further defined by reference to the following examples describing in detail the preparation of the compound and compositions of the invention. It will be apparent to those skilled in the art that many modifications, both to materials and methods, may be practiced without departing from the scope of the invention.

5 EXAMPLES

5.1. Example 1

Chiral Salt Resolution of R(−)-ketoprofen

A sample of 126 g (500 mmol) of (R,S)-ketoprofen was combined with 800 g of methyl isobutyl ketone, heated to 40° C. and stirred until the mixture dissolved. The solution was treated with 74 g (500 mmol) of cis-(1S,2R)-1- aminoindan-2-ol, mixed for 30 minutes, seeded with 20 g of R(−)-ketoprofen cis-(1S,2R)-1-aminoindan-2-ol diastereomer salt and held at 40° C. for 30 minutes. The mixture was cooled to 25° C. over the course of 4 hours and further cooled to 15° C. over the course of 1 hour and then held at 15° C. for 18 hours. The solids that formed were collected by filtration and dried under vacuum to yield 86 g of R(−)-ketoprofen cis-(1S,2R)-1-aminoindan-2-ol diastereomer with an R(−)-ketoprofen diastereomeric excess of 97%. The acid was released from the diastereomer salt by combining the solid with equal amounts (315 g) of ethyl acetate and aqueous (12 weight percent) sulfuric acid. After mixing, the aqueous phase was separated (saved for recovery of aminoindanol) and the organic phase washed twice with equal volumes of water. The organic phase was evaporated under vacuum. The weight of the solid residue was 54 g (66% yield based on available enantiomer and corrected for added seed diastereomer salt crystals) corresponding to R(−)-ketoprofen of 97% enantiomeric excess.

5.2. Example 2

Enzymatic Resolution of R(−)-ketoprofen

A. Synthesis of Dimethylethanolamine Ester

Racemic ketoprofen (0.5 moles) was added to thionyl chloride (1.0 moles) in a flask fitted with a drying tube. Dimethylformamide (0.25 ml) was added to the reaction mixture and the mixture was stirred and warmed until the ketoprofen dissolved and gas evolution commenced. The heat was removed and the mixture was stirred at room temperature for 18 hours. The thionyl chloride was removed under reduced pressure and the oily residue of acid chloride slowly solidified.

The acid chloride was dissolved in tetrahydrofuran (125 ml) and added to a solution of N,N-dimethylethanolamine (1.0 moles) in tetrahydrofuran (500 ml) cooled to 0° C. in a flask equipped with a drying tube. After the addition, the reaction mixture was stirred at room temperature for 18 hours. A saturated aqueous solution of potassium carbonate (500 ml) was added to the reaction mixture and the resulting organic layer was removed. The aqueous layer was extracted with diethyl ether (2×250 ml) and the organic layers were combined, washed with a saturated aqueous solution of sodium chloride, dried over potassium carbonate and the solvent removed under reduced pressure. The product was isolated as a colorless viscous oil.

B. Quaternization of the N,N-Dimethylethanolamine Ester

The resulting N,N-dimethylethanolamine ester was dissolved in diethyl ether (500 ml) and cooled to 0° C. A solution of dimethyl sulfate (0.36 moles) in diethyl ether (500 ml) was added to the cooled solution and the resulting solution was stirred at room temperature for 18 hours. The resulting solid material was removed by filtration, washed with diethyl ether and dried under vacuum to yield the N,N,Ntrimethylethanolammonium ester of ketoprofen (ketoprofen choline ester) as a white solid.

C. Enzymatic Transesterification of the Racemic Ketoprofen Choline Ester

The choline ester (0.36 moles) was dissolved in 0.2 M sodium phosphate buffer (900 ml, pH 7.0). To this solution was added methanol (100 ml) and Protease type XXVII (3 gm) which is available commercially from Sigma Chemical Co., St. Louis, Mo. The reaction was allowed to stir gently at room temperature for 24 hours. The reaction mixture was extracted with diethyl ether (2×250 ml) and the organic layer was reserved. The aqueous layer was adjusted to pH 2 by the addition of concentrated sulfuric acid and the resulting mixture was washed with ether (2×150 ml). The aqueous layer was concentrated under reduced pressure and the volume was adjusted to 900 ml by the addition of 0.2 M sodium phosphate buffer (pH 7.0). To this solution was added methanol (100 ml) and Protease type XXVII (2 gm). The reaction was allowed to stir gently at room temperature for 24 hours. The reaction mixture was extracted with diethyl ether (2×250 ml) and this organic layer was combined with the layer reserved from the first enzymatic reaction. The combined ether layers were dried over magnesium sulfate and the solvent removed under reduced pressure to leave crude R(−)-ketoprofen methyl ester, which was dried under vacuum.

D. Preparation of R(−)-ketoprofen

The crude ester was combined with ethanolic potassium hydroxide solution (pH 13) and the resulting mixture was stirred for 1 hour at room temperature.

The resulting solution was adjusted to pH 2 by the addition of hydrochloric acid. The resulting mixture was extracted with diethyl ether and the combined ether solutions were dried over magnesium sulfate and the solvent removed under reduced pressure to leave crude R(−)-ketoprofen. The crude acid was recrystallized from diethyl ether to yield R(−)-ketoprofen.

5.3 Example 3

Evaluation of Neuropathic Pain

Tight ligation of the $L_5$ and $L_6$ spinal nerves in rats can be used to model neuropathic pain, as it produces signs of neuropathic dysesthesias, including tactile allodynia, thermal hyperalgesia and guarding of the affected paw. Such nerve ligation injury can be performed by the method described by Kim and Chung, *Pain,* 50(3):355–363 (1992). In this method, rats are anesthetized with halothane and the vertebrae over the L4 to S2 region are exposed. The $L_5$ and $L_6$ spinal nerves are exposed, carefully isolated, and tightly ligated with 4-0 silk suture distal to the dorsal root ganglion ("DRG"). After ensuring homeostatic stability, the wounds are sutured, and the rats allowed to recover in individual cages. Sham-operated rats are prepared in an identical manner except that the $L_5$ and $L_6$ spinal nerves are not ligated. Any rats which show signs of motor deficiency are not-used in the study.

Tactile allodynia and thermal hyperalgesia evaluations are performed using the ligated and sham-operated rats. R(−)-ketoprofen, or other test article or control, is administered to the rats prior to performing these evaluations.

Mechanical allodynia is determined in the manner described by Chaplan et al., *J. Neurosci. Methods,* 53(1):55–63 (1994), wherein the paw withdrawal threshold is determined in response to probing with calibrated von Frey filaments. In this method, the rats are suspended in cages having wire mesh floors. Von Frey filaments are applied perpendicularly to the plantar surface of the rat's paw until it buckles slightly, and is held for about 3 to 6 seconds. A positive response is indicated by a sharp or abrupt withdrawal of the paw. The 50% paw withdrawal threshold is determined by a non-parametric method, as is well known to those skilled in the art.

Thermal hyperalgesia is determined by focusing a radiant heat source onto the plantar surface of the affected paw of nerve-ligated or sham-operated rats. When a rat withdraws its paw, a photodetection devices halts the stimulus and the timer. A maximal cut-off time of 40 seconds is used to prevent tissue damage. Paw withdrawal latencies are thus determined to the nearest 0.1 second. The withdrawal latency of sham-operated rats is compared to those of nerve-ligated rats to measure the degree of hyperalgesia.

In addition, non-operated rats can be evaluated for central sensitization arising from a tonic nociceptive stimulus, such as formalin injection in to the hindpaw. For this evaluation, non-operated rats are allowed to acclimate to a flinching chamber for about 20 minutes. A flinching chamber comprises wood panels with Plexiglas floors and front panels to allow observation of the animal. A mirror is placed at about a 45° angle under the floor to facilitate viewing of the animal's hindpaws. The rats are given a subcutaneous injection of 50 μl of 2% formalin solution s.c. into the dorsum of the right hindpaw immediately after administration of the vehicle or test article. Animals are then returned to the flinching chambers for the duration of the experiment and observed for flinching behavior. Numbers of flinches observed are recorded in 5 minute intervals for 50 minutes beginning at the time of formalin injection. Data are recorded as mean flinches/5 minute bin for phase I (0 to 15 minutes) and phase II (20 to 50 minutes). The areas under the time-effect curves are calculated for each rat to allow statistical analyses.

5.4. Example 4

Evaluation of Tinnitus

Hamsters and rats experience major increases in spontaneous neural activity in the dorsal cochlear nucleus ("DCN") after exposure to agents known to induce tinnitus in humans, and thus may be used in tinnitus animal models. See, e.g., Zhang and Kaltenbach, *Neuroscience Letters,* 250(3) (1998); Kaltenbach et al., *Hearing Res.,* 124(1–2):78–84 (1998); and Meleca et al., *Brain Res.,* 750(1-2):201–213 (1997). This increased activity in the DCN displays a similar pattern to that exhibited by sound-evoked DCN activity, and suggests that the animals with agent-induced abnormality may be hearing a sound. See Kaltenbach and McCaslin, *Auditory Neuroscience,* 3/1:57–78 (1996). The effect of R(−)-ketoprofen on tinnitus can be evaluated by determining its affect on reversing the increase in spontaneous DCN activity in rats or hamsters.

In general, changes in spontaneous activity in the DCN is performed by exposing one ear (e.g., the left ear) of each animal to an intense 10 kHz tone at a level of 125 dB for a period of about 4 hours. After exposure, the animals are allowed to recover for about 4 weeks to permit stabilization of the induced increase in spontaneous DCN activity. After this recovery period, each animal is anesthetized and undergoes surgery to uncover the DCN ipsilateral to the exposed ear. Thereafter, a microelectrode is used to map the activity along the DCN surface. When the mapping is finished, the microelectrode is inserted into the DCN at the location which shows the highest increase in activity. The microelectrode is inserted to a depth of between about 130 microns to about 200 microns, and the activity at this test site is measure to give a baseline spontaneous rate.

After the baseline measurement is taken, R(−)-ketoprofen, or another test article or vehicle, is applied and the activity is then measured to give a drug-related change in DCN activity. The effect of the drug is determined by the difference between pre- and post-application activity measurements. After application of the test article and measurement of activity, the applied test article is aspirated off the surface of the DCN and an ACSF rinse or washout solution is applied. This same site is then tested with the same test article at several different concentrations, and the effect of the test article is again determined by taking the difference between pre- and post-application spontaneous DCN activity rates.

5.5. Example 5

Oral Formulation

Table 1 provides the ingredients for a tablet dosage form of optically pure R(−)-ketoprofen:

TABLE 1

| Component | Quantity per Tablet (mg) |
| --- | --- |
| R(−)-ketoprofen | 75 |
| Lactose | 125 |
| Corn Starch | 5.0 |
| Water (per thousand tablets) | 30.0ml* |
| Magnesium Stearate | 0.5 |

\* The water evaporates during manufacture.

The active ingredient (ie., R(−)-ketoprofen) is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets are coated by standard aqueous or nonaqueous techniques.

Another tablet dosage formulation suitable for use with the active ingredient of the invention is provided by Table 2:

TABLE 2

| | Quantity per Tablet (mg) | | |
| --- | --- | --- | --- |
| Component | Formula A | Formula B | Formula C |
| R(−)-ketoprofen | 20 | 40 | 100 |
| Lactose BP | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with lactose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by using different punches.

5.6. Example 6

Oral Formulation

Capsules of R(−)-ketoprofen suitable for the treatment of neuropathic pain or tinnitus are made using the ingredients provided in Table 3:

TABLE 3

| Formulation | Quantity per Capsule (mg) | | |
|---|---|---|---|
| | A | B | C |
| Ingredients | | | |
| R(−)-ketoprofen | 50.0 | 100.0 | 200.0 |
| Lactose | 48.5 | 148.5 | 48.5 |
| Titanium Dioxide | 0.5 | 0.5 | 0.5 |
| Magnesium Stearate | 1.0 | 1.0 | 1.0 |
| Fill Weight | 100.0 | 250.0 | 250.0 |

The active ingredient (i.e., R(−)-ketoprofen) is sieved and blended with the excipients. The mixture is filled into suitably sized two-piece hard gelatin capsules using suitable machinery. Other doses may be prepared by altering the ratio of R(−)-ketoprofen and pharmaceutically acceptable carrier, the fill weight and, if necessary, by changing the capsule size to suit.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating neuropathic pain in a mammal which comprises administering to a mammal in need of such treatment a therapeutically effective amount of substantially optically pure R(−)-ketoprofen, or a pharmaceutically acceptable salt, solvate, or clathrate thereof.

2. The method of claim 1 wherein the therapeutically effective amount of substantially optically pure R(−)-ketoprofen, or a pharmaceutically acceptable salt, solvate, or clathrate thereof, is between about 1 mg and about 2000 mg.

3. The method of claim 2 wherein the therapeutically effective amount of substantially optically pure R(−)-ketoprofen, or a pharmaceutically acceptable salt, solvate, or clathrate thereof, is between about 5 mg and about 1500 mg.

4. The method of claim 3 wherein the therapeutically effective amount of substantially optically pure R(−)-ketoprofen, or a pharmaceutically acceptable salt, solvate, or clathrate thereof, is between about 10 mg and about 1000 mg.

5. The method of claim 1 wherein the substantially optically pure R(−)-ketoprofen comprises less than about 10% by weight S(+)-ketoprofen.

6. The method of claim 5 wherein the substantially optically pure R(−)-ketoprofen comprises less that about 5% by weight S(+)-ketoprofen.

7. The method of claim 6 wherein the substantially optically pure R(−)-ketoprofen comprises less than about 1% by weight S(+)-ketoprofen.

8. The method of claim 1 wherein the neuropathic pain is a central neuropathy.

9. The method of claim 8 wherein the central neuropathy arises from damage or disease of the spinal cord, brainstem, thalamus, or cerebellum.

10. The method of claim 1 wherein the neuropathic pain is a peripheral neuropathy.

11. The method of claim 10 wherein the peripheral neuropathy is a thoracic outlet obstruction syndrome, a compression and entrapment neuropathy, or Guillain-Barré syndrome.

12. The method of claim 11 wherein the compression and entrapment neuropathy is selected from the group consisting of ulnar nerve palsey, carpal tunnel syndrome, peroneal nerve palsey, and radial nerve palsey.

13. The method of claim 1 wherein the mammal is human.

* * * * *